US008588363B2

(12) United States Patent
Flohr

(10) Patent No.: US 8,588,363 B2
(45) Date of Patent: Nov. 19, 2013

(54) DUAL-SOURCE CT DEVICE AND METHOD FOR SPIRAL SCANNING

(75) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 91 days.

(21) Appl. No.: 13/249,293

(22) Filed: Sep. 30, 2011

(65) Prior Publication Data
US 2012/0082289 A1    Apr. 5, 2012

(30) Foreign Application Priority Data

Sep. 30, 2010   (DE) .......................... 10 2010 041 772

(51) Int. Cl.
*A61B 6/00*    (2006.01)
(52) U.S. Cl.
USPC ................................................... 378/9; 378/8
(58) Field of Classification Search
USPC ......................................................... 378/8, 9
See application file for complete search history.

(56) References Cited

U.S. PATENT DOCUMENTS

| 2003/0076920 A1 | 4/2003 | Horinouchi |
| 2004/0213371 A1* | 10/2004 | Bruder et al. ...................... 378/9 |
| 2005/0089134 A1* | 4/2005 | Bruder et al. ...................... 378/9 |
| 2005/0111622 A1* | 5/2005 | Bruder et al. .................... 378/95 |
| 2005/0111623 A1* | 5/2005 | Bruder et al. .................... 378/95 |
| 2007/0025499 A1* | 2/2007 | Bruder et al. ...................... 378/9 |
| 2007/0098136 A1* | 5/2007 | Lutz ................................... 378/9 |
| 2007/0280407 A1* | 12/2007 | Kunze et al. ....................... 378/4 |
| 2009/0141855 A1 | 6/2009 | Bruder |

OTHER PUBLICATIONS

German priority document DE 10 2010 041 772.6 filed Sep. 30, 2010 (not yet published).

* cited by examiner

*Primary Examiner* — Alexander H Taningco
(74) *Attorney, Agent, or Firm* — Harness, Dickey & Pierce

(57) ABSTRACT

At least one embodiment of the invention relates to a dual-source CT device with two focus-detector systems arranged on a gantry offset at an angle n and at least one embodiment relates to a method for spiral scanning and for the reconstruction of tomographic image data of a patient. In at least one embodiment, the detectors have a different z-width in the system axis direction and a computer system with a program memory with at least one computer program, by which during operation the dual-source CT device controls a spiral scanning of a patient and CT-image data is reconstructed from absorption data obtained from both unequally wide detectors, wherein in particular a spiral is controlled with a couch feed rate per rotation, which is greater than the maximum couch feed rate possible with the narrower detector.

18 Claims, 2 Drawing Sheets

DUAL-SOURCE CT DEVICE AND METHOD FOR SPIRAL SCANNING

PRIORITY STATEMENT

The present application hereby claims priority under 35 U.S.C. §119 on German patent application number DE 10 2010 041 772.6 filed Sep. 30, 2010, the entire contents of which are hereby incorporated herein by reference.

FIELD

At least one embodiment of the invention generally relates to a dual-source CT device with two focus-detector systems arranged on a gantry offset at an angle and/or a method for spiral scanning of a patient with the dual-source CT device.

BACKGROUND

Dual-source CT devices with two or three focus-detector systems arranged on a gantry offset at an angle and methods for the spiral scanning of a patient with these devices including the reconstruction method for the generation of image data sets from the attenuation data thereby obtained, in particular also within the framework of a EKG-triggered scanning and data collection, are generally known.

In the case of all known dual-source CT devices with a rotating gantry and a method for scanning with these devices the problem arises that to date it has thus far not been possible in practice to scan a heart beating at approximately normal physiological frequency completely within a cardiac rest phase. If, however partial image data from a number of successive cardiac cycles is combined to form a complete image data record of the heart, then image artifacts almost always occur at the interfaces of the image data.

SUMMARY

At least one embodiment of the invention is directed to identifying a dual-source CT device with two focus-detector systems arranged on a gantry offset at an angle and/or a method for spiral scanning of a patient with the dual-source CT device, wherein at a cost outlay feasible in practice with series production, the heart of a patient at a cardiac frequency of considerably more than 60 beats per minute can be completely scanned within the rest phase of a cardiac cycle with the aid of spiral scanning.

Advantageous embodiments of the invention form the object of subordinate claims.

In EKG-correlated cardiac imaging dual-source CT devices enable an extremely high temporal resolution of a quarter of the rotation time of the gantry, as two detectors offset at 90°—of the same width in the system axis direction—acquire data simultaneously from complementary angles. The temporal resolution is achieved in that partial images are combined from quarter rotation data sets acquired in parallel. In the case of non-cardio applications, this high temporal resolution is maintained, if as in cardio-mode, partial images are combined from quarter rotation data sets acquired in parallel. As the reconstruction is not EKG-correlated, the couch feed rate and thus the pitch are significantly increased. Typically, a dual-source CT device has a detector with reduced length in the peripheral direction, thus a limited field of view. If reconstruction only takes place in this limited field of view, for example for infant records, the pitch can even be significantly further increased.

For a prescribed collimation N×S with N lines and a line width of S and a prescribed pitch, the distance b of the first and last detector line after a partial rotation can be specified with $\Delta\alpha=\pi$:

$$b_{min}(\pi) = \frac{(\pi + 2\beta_{max}) \cdot \text{pitch} \cdot N \cdot S}{2\pi} - (N-1) \cdot S \cdot \cos(\beta_{max})$$

Here, $\beta_{max}$ indicates the half fan angle. If the pitch selected is too high, then depending on the parallel coordinates gaps arise in the volume scanning. The volume scanning is then free from gaps, if the following applies:

$$b_{min}(\pi) \leq S \cdot N/2$$

From these two equations it is possible to derive the condition relating to the maximum pitch with:

$$\text{pitch}_{max} \leq \frac{(N/2 + \cos(\beta_{max})) \cdot (N-1) \cdot 2\pi}{N \cdot (\pi + 2\beta_{max})}$$

In the limited field of view it is thus possible to set a significantly higher pitch, if the reconstruction angle is $\pi/2$. Moreover the high temporal resolution is retained.

In at least one embodiment a method thus arises, in which in the case of dual-source CT devices, the couch feed rate with spiral CT recordings can be significantly increased compared with single-source CT devices. Here a dual-source CT device with two detectors of equal width in the patient longitudinal direction, system axis direction or z-direction is assumed, and the possible z-feed or pitch thereby attainable compared with a single-source CT device with a detector of the same width in the z-direction. What is shown here is that instead of maximum pitch values of about 1.5 in the case of a single-source CT device, depending on the reconstructed field of view a maximum pitch of 3.2-3.4 can be realized with a dual-source CT device. Pitch is the feed per rotation divided by the collimated width of the detector in the z-direction. In the case of a detector with 64×0.6 mm collimation as an example, the collimated width in the z-direction—also known as the z-width—is 38.4 mm.

In the case of the maximum possible pitch with a dual-source CT device, data from around a quarter rotation per detector is used for image reconstruction. The temporal resolution of the images generated with this scan mode thus amounts to around one quarter of the rotation time of the dual-source CT device. This method is thus suitable for very rapid volume scans with a high temporal resolution. At the same time it is also known to use this method together with EKG-triggering in such a way that the data recording starts at a z-position selectable by the user—for example the heart base—in a phase of the cardiac cycle of the patient selectable by the user.

In the case of sufficiently great z-width of the two detectors—e.g. 64×0.6 mm per detector—it is thus possible to record the whole heart of the patient in a prescribed cardiac phase in just one cardiac cycle. In the case of two detectors with in each case 64×0.6 mm collimation and 0.28 s rotation time for example, the maximum couch feed rate with pitch 3.2-3.4 is around 430-460 mm/s. The heart with a z-extension of around 12 cm can thus be covered in about 0.26-0.28 s. Added to this is a recording time of about 75 ms in this example, corresponding to a total data recording time of about 0.34-0.36 s. This time is sufficient to map the heart at low heart rates in the diastolic, that is the rest phase, free from motion artifacts.

This method is employed as the so-called "Flash-Spiral" in the applicant's CT device of the type SOMATOM Definition Flash. Nevertheless the heart rate for this method in the case of two detectors each with 64×0.6 mm collimation as in "Definition Flash" must be very low, that is to say typically, according to clinical experience to date, below 60 beats per minute. With higher heart rates, the whole data recording time is too long, and parts of the heat volume are recorded in moving heart phases, which leads to motion artifacts and thus to results which are only of limited clinical usefulness.

It is basically possible, by way of further reduction of the rotation time of the scanner, to increase the feed rate, in order to reduce the recording time for a heart, although this is only possible with considerable mechanical effort and at considerable cost. A further obvious option is widening of both detectors in the z-direction. Thus two detectors with, for example, 128×0.6 mm collimation instead of 64×0.6 mm collimation would theoretically permit a doubling of the feed rate. However in this case the costs for the CT device would rise disproportionately, because the detectors are typically the most expensive component of a CT device, and the costs rise in a linear manner with the z-width of the detector.

The inventor has, however, recognized that it is sensible to equip a dual-source CT device with two detectors which are unequally wide in the z-direction, that is to make just one detector wider. For example the z-width of a detector A at $B_1$=64×0.6 mm can be left as it is, while the detector B is increased to a z-width of $B_2$=128×0.6 mm. With this arrangement with two detectors A and B of width $B_1$ and $B_2$, and $B_2 > B_1$, it is possible significantly to increase the maximum couch feed rate compared with a dual-source CT device with two detectors of width $B_1$ with the same width in the z-direction, without at the same time having to make both detectors wider.

According to at least one embodiment of the invention, for example the detector A $N_q^1$ has detector lines of collimated width S and the detector B $N_q^2$ detector lines of collimated width S, with $N_q^2 > N_q^1$. The pitch p can be defined in relation to the entire z-width $N_q^1 \cdot S$ of the detector A which is narrower in the z-direction. By means of standard azimuthal rebinning of the attenuation data recorded in fan beam geometry, parallel data with specific parallel projection angles θ is produced. If below—as is customary—we examine a "virtual detector" in the center of rotation in parallel geometry, this gives a maximum possible pitch $p_{max}$ as a result of the requirement that the ray at the edge of the field of view of the upper detector line of the detector B with the parallel coordinate $b_{max} = -R_F \beta_{max}$ and the line number $q_2 = 0$, and the complementary ray at the edge of the field of view of the lowest detector line of the detector A with the parallel—coordinate $\tilde{b}_{max} = R_F \beta_{max}$ and the line number $q_1 = N_q^1 - 1$, after a quarter rotation of the measuring system in the z-direction are less than a collimated layer thickness S apart, in order to enable a well defined spiral interpolation. $\beta_{max}$ is here the maximum fan angle in the desired field of view, $R_F$ is the distance of the tube focus from the center of rotation of the CT-scanner.

For the corresponding z-positions of these rays for detector A, the following is derived $$z^A(\tilde{b}_{max}, N_q^1 - 1) = \left(\frac{1 - N_q^1}{2}\right) S\cos\beta_{max} + z_{rot}\frac{\beta_{max}}{2\pi}$$

and for the detector B $$z^B(b_{max}, 0) = \left(\frac{N_q^2 - 1}{2}\right) S\cos\beta_{max} - z_{rot}\frac{\beta_{max}}{2\pi}.$$

$z_{rot}$ is the feed rate per rotation in mm.

From the condition $$\left(z^A(\tilde{b}_{max}, N_q^1 - 1) + \frac{z_{rot}}{4}\right) - z^B(b_{max}, 0) =$$

$$\left(1 - \frac{N_q^1 + N_q^2}{2}\right) S\cos\beta_{max} + z_{rot}\left(\frac{2\beta_{max} + \frac{\pi}{2}}{2\pi}\right) \leq S$$

with $z_{rot} = N_q^1 \cdot S \cdot p$ following immediately, $$p_{max} = \frac{2\pi\left(1 + \left(\frac{N_q^1 + N_q^2}{2} - 1\right)\cos\beta_{max}\right)}{N_q^1\left(2\beta_{max} + \frac{\pi}{2}\right)},$$

wherein the pitch p relates to the narrower detector A with $N_q^1$ lines.

By comparison with a dual-source CT device with two equally wide detectors with $N_q^2 = N_q^1$ the maximum pitch is higher by the factor $$F(N_q^2, N_q^1) = \frac{1 + \left(\frac{N_q^1 + N_q^2}{2} - 1\right)\cos\beta_{max}}{1 + (N_q^1 - 1)\cos\beta_{max}}$$

In the center of rotation, for $\beta_{max} = 0$, $$F(N_q^2, N_q^1) = \frac{N_q^1 + N_q^2}{2N_q^1}$$

applies.

In the top example, the pitch for $N_q^2 = 2N_q^1$ that is in the center of rotation, could be increased by the factor 3/2. Instead of pitch 4, as in the case of two detectors with $N_q^2 = N_q^1$, pitch 6 in the center of rotation would now be possible.

In the case of a dual-source CT device with two unequally wide detectors in the z-direction, with 64×0.6 mm collimation and 128×0.6 mm collimation, and 0.28 s rotation time, the maximum couch feed rate at pitch 4.8 amount to around 660 mm/s. With this modified arrangement, the heart with a z-extension of about 12 cm can be covered in only in only about 0.18 s. At least one embodiment of the inventive device is thus considerably faster than a dual-source CT device with two detectors of the same size in the z-direction, each with 64×0.6 mm collimation, which requires 0.26-0.28 s for this.

Dual-source CT devices with two detectors of equal width in the z-direction use at maximum pitch in each case about one quarter rotation in data in parallel geometry per measurement system for the image reconstruction. The temporal resolution thus amounts to about one quarter of the rotation time of the dual-source CT device. In the case of dual-source CT devices with two unequally wide detectors in the z-direction, the data intervals used for reconstruction are unsymmetrical. The semi-rotation interval necessary for image reconstruction in parallel geometry can thus be so divided that the wider detector in the z-direction contributes more and the narrower detector in the z-direction less. The detector B then contributes an approximate data interval of length $$\frac{N_q^2}{N_q^1+N_q^2}\pi$$

for image reconstruction, detector A on the other hand a data interval of length $$\frac{N_q^1}{N_q^1+N_q^2}\pi.$$

In the top example with $N_q^2=128$ and $N_q^1=64$ the wider detector B thus contributes about 120° to the image reconstruction, detector A on the other hand only about 60°. As the temporal resolution is given by the longer of the data intervals, then with 0.28 s rotation time, the temporal resolution is no longer 75 ms, but around 100 ms. This slight deterioration of the temporal resolution is however in practice less significant than the reduction of the whole recording time.

Overall, the entire data recording time for recording of the heart with a length of 12 cm with the asymmetrical arrangement and with wide detectors of different lengths amounts to about 0.18 s+0.1 s=0.28 s, while with the symmetrical arrangement with two identical detectors it is about 0.34-0.36 s. The heart volume can thus be covered with an overall significantly lower recording time, and it is thus possible, even in the case of higher heart rates, to map the heart in the low-motion rest phase without artifacts.

With this recording technology proposed here for a dual-source CT device with two unequally wide detectors in the z-direction it is possible to achieve wider applicability of the flash-spiral described in the introduction for patients with higher heart rates too, because the maximum couch feed rate can be further increased and thus the entire data recording time further reduced. The increase in the maximum couch feed rates can be achieved without both detectors having to be widened in the z-direction. Otherwise than expected, it is sufficient to widen one detector only. The cost of the CT device can thereby be significantly reduced.

According to the basic concept illustrated above, the inventor is proposing an improved dual-source CT device and an improved method for spiral scanning of a patient with such a dual-source CT device.

At least one embodiment of the inventive dual-source CT device has two focus-detector systems arranged on a gantry offset at an angle, wherein the detectors have a different z-width in the system axis direction, and a computer system with a program memory with at least one computer program, by which during operation the dual-source CT device controls a spiral scanning of a patient and reconstructs CT-image data from the absorption data obtained from the two unequally wide detectors.

In an advantageous embodiment of the dual-source CT device, it is proposed that the detectors have a different number of detector lines and the computer program for control of the dual-source CT device is embodied such that during operation it controls a spiral with a maximum pitch $p_{max}$ of $$p_{max}=\frac{2\pi\left(1+\left(\frac{N_q^1+N_q^2}{2}-1\right)\cos\beta_{max}\right)}{N_q^1\left(2\beta_{max}+\frac{\pi}{2}\right)},$$

wherein:
$N_q^1$ is the number of the detector lines of the narrower detector,
$N_q^2$ is the number of the detector lines of the wider detector, and
$\beta_{max}$ is the maximum fan angle of the narrower detector.

Furthermore, the narrow detector can be embodied to be longer in the peripheral direction than the detector which is wider in the system axis direction.

Additionally, the dual-source CT device can be so embodied that both detectors have the same number of detector elements and/or the same effective detector surface. Basically, wafers carrying identical and the same number of detector elements can be used for this, which merely need to be put together in a different arrangement for different formats of detectors. The read-out electronics too can remain the same in this situation, except for changes to the software.

The wider detector can also preferably be twice as wide as the narrower detector.

In addition to the inventive dual-source CT device, in at least one embodiment the inventor is also proposing a method for spiral scanning and for the reconstruction of tomographic image data of a patient with such a dual-source CT device with two focus-detector systems arranged on a gantry offset at an angle with detectors of different widths in the system axis direction, wherein in each case a cone of rays forms between the focus and detector, which has the following method steps:

Execution of the spiral scanning, wherein a pitch is set, in which—in relation to virtual detectors formed by the focus-detector systems in the center of rotation—a corner of the wide detector, which is formed from the rear row of detector elements in the direction of rotation and the front line of detector elements in the z-direction, overlaps the rear detector line of the narrow detector in the direction of feed, reconstruction of tomographic image data from attenuation data stemming from both focus-detector systems, wherein the data required for reconstruction stems in each case from both detectors and the amount of data from the wide detector outweighs the data from the narrow detector, Output of at least one tomographic image data set from the mixed data of the narrow and wide detectors.

Advantageously, the spiral scanning and/or detector data selection can be performed EKG-triggered.

Further advantageously, the ratio of the detector data used for reconstruction can be matched to the ratio of detector lines of both detectors.

It can also be favorable if relative to the narrow detector twice as many detector lines are used for the wide detector. Additionally, the detectors can be arranged on the gantry and/or the direction of rotation of the gantry selected in such a way that the narrow detector follows the wide detector during scanning.

At least one embodiment of the invention thus discloses a dual-source CT device with two detectors which are unequally wide in the z-direction, which form the virtual detectors A with the collimated z-width $B_1$ and a line number $N_q^1$ and B with the collimated z-width $B_2$ and a line number $N_q^2$, with $B_2>B_1$. This dual-source CT device can be operated for a spiral recording with a maximum couch feed rate which is significantly increased relative to a dual-source CT device with two detectors of the same width in the z-direction, of width $B_1$. The maximum value of the pitch for a high quality spiral image reconstruction in relation to the narrower detector in the z-direction is with effective layer thicknesses of a full width at half maximum, which amounts to not more than approximately 1.3 times the collimated layer thickness, is significantly increased, by the factor $$F(N_q^2, N_q^1) = \frac{N_q^1 + N_q^2}{2N_q^1}$$

compared with a dual-source CT device with detectors of the same width in the z-direction, width $B_1$, with a line number $N_q^1$. An EKG-controlled spiral recording of periodically moving organs can also be performed with this device, wherein the whole heart is to be scanned in a cardiac cycle.

An image reconstruction with a dual-source CT device with two unequally wide detectors A and B in the z-direction, of widths $B_1$ and $B_2$, with $B_2 > B_1$, is further proposed, wherein according to the described data interval necessary for the mage reconstruction at maximum pitch or maximum couch feed rate can be divided up such that the detector wider in the z-direction contributes more, and the detector narrower in the z-direction less. The detector B then contributes a data interval of approximately $$\frac{N_q^2}{N_q^1 + N_q^2}\pi$$

to the image reconstruction, while the detector A contributes a data interval of $$\frac{N_q^1}{N_q^1 + N_q^2}\pi.$$

BRIEF DESCRIPTION OF THE DRAWINGS

Embodiments of the invention are described in detail below on the basis of the figures, wherein only the features necessary for understanding of the invention are represented. The following reference characters are used: 1: Dual-source CT device; 2: First X-ray tube; 3: Wide, short detector; 4: Second X-ray tube; 5: Narrow, long detector; 6: Gantry housing; 7: Patient; 8: Traveling patient couch; 9: System axis; 10: Computer; 11: Contrast medium applicator; 12: EKG-scanner line; A: Virtual narrow, long detector; B: Virtual wide, short detector; $Prg_1$ to $Prg_n$: Computer programs.

Wherein individually.

DETAILED DESCRIPTION OF THE EXAMPLE EMBODIMENTS

Figure 1:
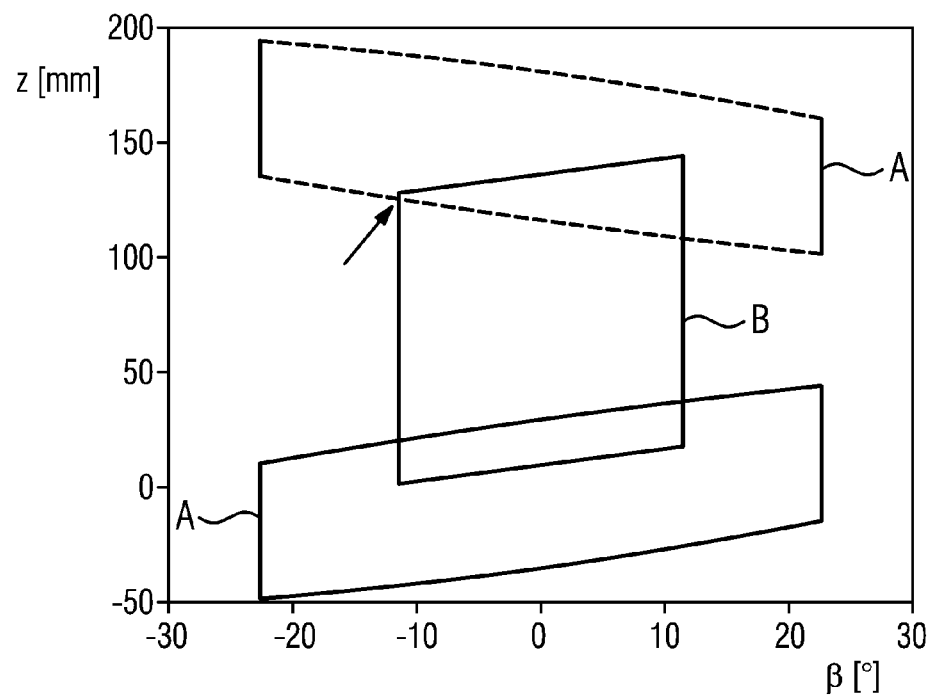
FIG. 1: Represents the virtual detectors of different widths of an inventive dual-source CT device in the center of rotation of the gantry.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows two virtual detectors A and B in the center of rotation of an inventive dual-source CT device. The detector B is twice as wide as detector A in the z-direction, wherein the narrower detector A has been projected from opposite directions too in the center of rotation of the gantry. The pitch in this example is p=4.8, in relation to the narrower detector A. The maximum pitch $p_{max}$, to be more precise the maximum possible pitch without data gaps arising with spiral scanning, is derived from the condition that rays at the edge of the field of view of detector B and complementary rays from detector A are less than a layer thickness S apart. The arrow points to the corner of the wide detector, which is formed from the rear row of detector elements in the direction of rotation and the front line of detector elements in the z-direction and just overlaps the rear detector line of the narrow detector in the direction of feed. Thus with the maximum pitch a feed is selected at which as little redundant attenuation data is generated with as few data gaps as possible, wherein data redundancy with oppositely directed rays with the same coverage is assumed.

With a maximum fan angle of about 11°, equivalent to a cardio-field of view of some 220 mm in diameter, a pitch of approximately 4.8 in relation to the smaller detector can be selected, instead of about 3.2 in the case of two detectors of the same size.

Figure 2:
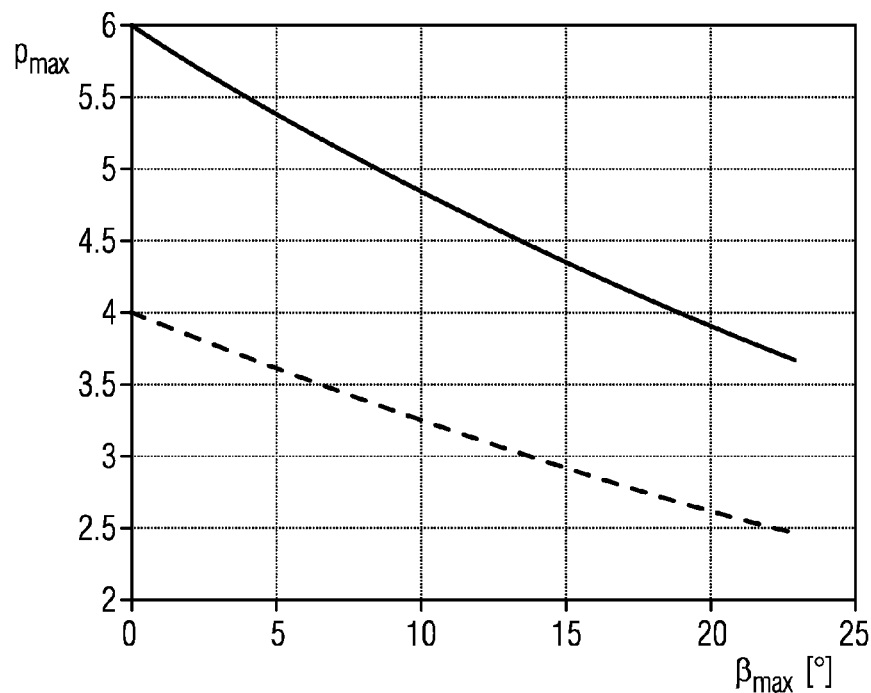
FIG. 2: Represents the course of the maximum possible pitch against the maximum fan angle.

If—as shown in FIG. 2—the maximum possible pitch $p_{max}$ is applied to the ordinate as a function of the greatest fan angles $\beta_{max}$ on the abscissa for a dual-source CT device with two detectors of different extensions in the z-direction with $N_q^2=128$ lines and $N_q^1=64$ lines, this gives a course corresponding to the continuous line. For comparison, the course of the maximum pitch $p_{max}$ is applied as a function of the greatest fan angle $\beta_{max}$ for a dual-source CT device with two detectors which are the same in the z-direction with $N_q^2=64$ and $N_q^1=64$. The maximum pitch with detectors of different widths is thus considerably higher.

Figure 3:
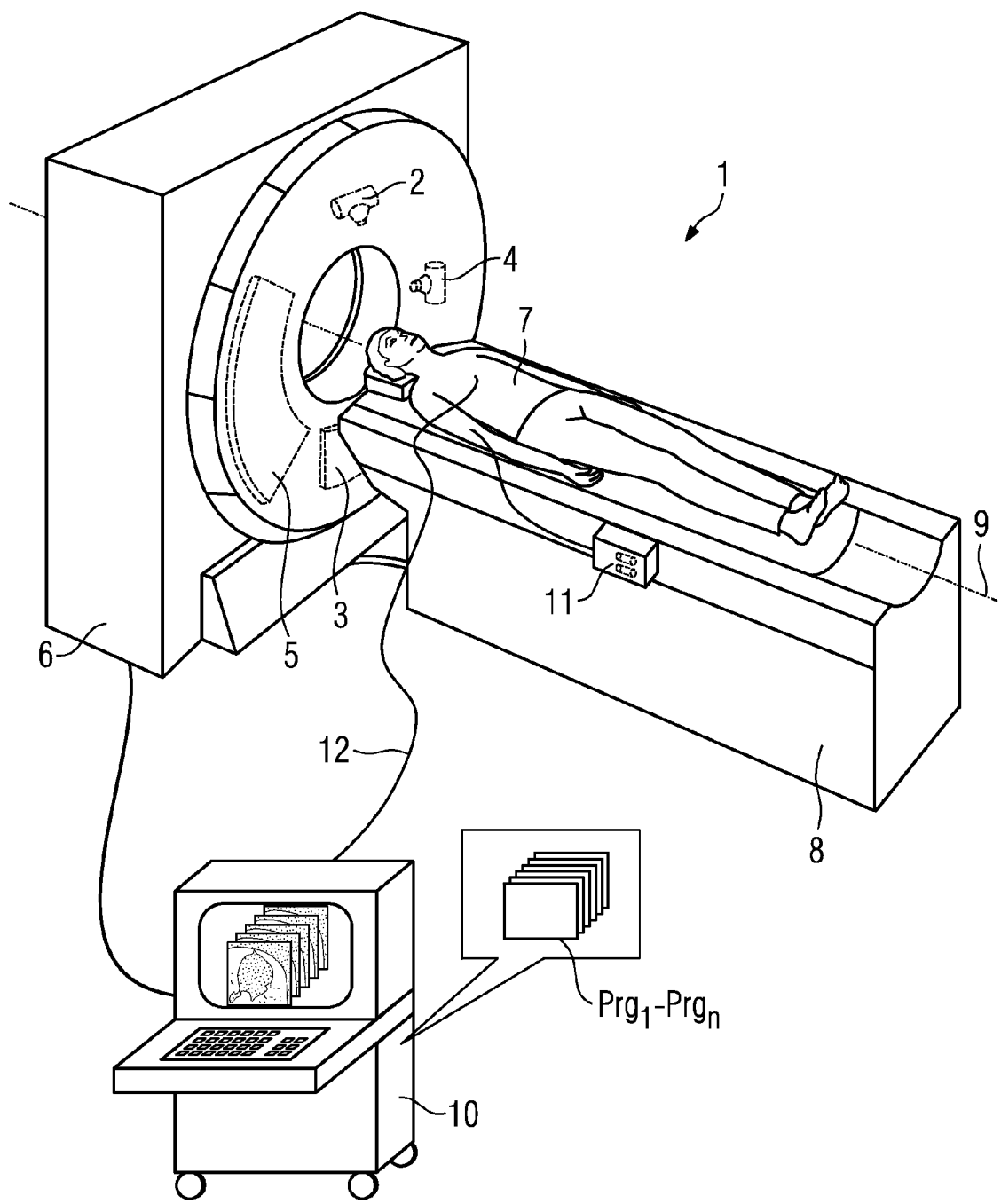
FIG. 3: Shows the inventive CT device with two detectors of different widths.

FIG. 3 finally shows an example of an inventive dual-source CT device 1 with two focus-detector systems, which is equipped for execution of an embodiment of the inventive method. The two focus-detector systems equipped with detectors of different widths in the system axis direction and of different lengths in the peripheral direction are formed by a first X-ray tube 2 with an oppositely located wide and short detector 3—which form the virtual detector B according to the example represented above—and by a second X-ray tube 4 with a further oppositely located narrow but long detector 5—which generates the virtual detector A. The focus-detector systems are arranged on the gantry offset at an angle of 90° and are located in the gantry housing 6. The patient 7 is placed on the traveling patient couch 8, which in the case of the inventive examination during the scans is fed along the system axis 9 through the centrally arranged field of view, so that a spiral scanning with a large pitch takes place in relation to the patient.

An EKG-analysis can also be provided for the EKG-triggered scanning in the computer 10, which with the aid of the EKG-scanner line 12 attached to the patient analyses the EKG-signal from the patient 7 and can control the CT device accordingly. Additionally, a contrast medium applicator 11 is also located on the patient couch 8, which can perform the corresponding application of a contrast medium, under the control of the computer 10 if required.

The entire system is controlled by computer programs $Prg_1$-$Prg_n$, which are stored in a memory, which the computer 10 can access. Also located in this memory is program code, which can perform the inventive scanning and analysis of the detector data including its reconstruction during operation of the system.

To summarize, an embodiment of the invention thus discloses a dual-source CT device with two focus-detector systems arranged on a gantry offset at an angle n and a method for spiral scanning and for the reconstruction of tomographic image data of a patient, wherein the detectors have a different z-width in the system axis direction, and a computer system with a program memory with at least one computer program, by which during operation the dual-source CT device controls a spiral scan of a patient and reconstructs CT-image data from the absorption data obtained from both unequally wide detectors, wherein in particular a spiral with a couch feed rate per rotation is controlled, which is greater than the maximum couch feed rate possible with the narrower detector.

It is also pointed out that because of the high temporal resolution desired the scans and image reconstructions described here primarily relate to complete scans over an angular range of 180° plus the fan angle (=180°-scanning) and are accordingly detector data from a projection interval of in total 180° per image (=180°-image) is used with the reconstructions.

It is obvious that the aforementioned features of the invention can not only be used in the respectively specified combination, but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Dual-source CT device, comprising:
two focus-detector systems, arranged on a gantry offset at an angle n, at least one detector in one of the two focus-detector systems having a different z-width in a system axis direction than at least one detector in the other of the two focus-detector systems; and
a computer system, including a program memory including at least one computer program, to, during operation the dual-source CT device, control a spiral scanning of a patient and reconstruct CT-image data from absorption data obtained from the two unequally wide detectors.

2. The dual-source CT device as claimed in claim 1, wherein the at least one detector of the two focus-detector systems includes a different number of detector lines and wherein the at least one computer program, for control of the dual-source CT device, is embodied such that during operation it controls a spiral with a couch feed rate per rotation which is greater than a maximum couch feed rate possible with the at least one relatively narrower detector.

3. The dual-source CT device as claimed in the preceding claim 1, the at least one detector of the two focus-detector systems includes a different number of detector lines and wherein the at least one computer program for control of the dual-source CT device is embodied such that during operation, it controls a spiral with a pitch of $$p_{max} = \frac{2\pi\left(1 + \left(\frac{N_q^1 + N_q^2}{2} - 1\right)\cos\beta_{max}\right)}{N_q^1\left(2\beta_{max} + \frac{\pi}{2}\right)},$$

wherein:
$N_q^1$ corresponds to the number of detector lines of the at least one relatively narrower detector,
$N_9^2$ corresponds to the number of detector lines of the at least one relatively wider detector, and
$\beta_{max}$ is the maximum fan angle of the at least one relatively narrower detector and if applicable, relatively longer detector.

4. The dual-source CT device as claimed in claim 1, wherein means are provided, by which the data recording is triggered by a physiological signal of the patient.

5. The dual-source CT device as claimed in claim 4, wherein the physiological signal of the patient is an EKG.

6. The dual-source CT device as claimed in claim 1, wherein the at least one relatively narrow detector is twice the length in the peripheral direction than the at least one detector which is relatively wider in the system axis direction.

7. The dual-source CT device as claimed in claim 1, wherein each of the two focus-detector systems include at least one of
a same number of detector elements, and
a same effective detector area.

8. The dual-source CT device as claimed in claim 1, wherein the relatively wider at least one detector is twice as wide as the relatively narrow at least one detector.

9. The dual-source CT device as claimed in claim 1, wherein the at least one relatively wider detector is arranged ahead of the at least one relatively narrower detector in a direction of rotation.

10. A method for spiral scanning and reconstruction of the tomographic image data of a patient with a dual-source CT device with two focus-detector systems arranged on a gantry offset at an angle n, one of the two focus-detector systems including at least one detector of a different width in the system axis direction than at least one detector of the other of the two focus-detector systems, wherein a cone of rays forms respectively between a focus and the at least one detector of each of the two focus-detector systems, the method comprising:
executing the spiral scanning, wherein a pitch is set in which, in relation to virtual detectors respectively formed by each of the two focus-detector systems in a center of rotation, a corner of a relatively wider of the virtual detectors, formed from a rear row of detector elements in a direction of rotation and a front line of detector elements in a z-direction, overlaps a rear detector line of the relatively narrow of the virtual detectors in a direction of feed;

reconstructing tomographic image data from attenuation data stemming from both of the two focus-detector systems, wherein data for reconstruction is selected, in each case, from both of the virtual detectors and wherein a volume of data from the relatively wide detector outweighs data from the relatively narrow detector; and outputting at least one tomographic image data set of reconstructed tomographic image data from mixed data from the relatively narrow and relatively wide virtual detectors.

11. The method as claimed in claim 10, wherein execution of at least one of the spiral scanning and detector data selection is EKG-triggered.

12. The method as claimed in claim 11, wherein a ratio of the detector data selected and used for reconstruction is matched to a ratio of detector lines of both virtual detectors.

13. The method as claimed in claim 11, wherein twice as many detector lines are used for the relatively wide detector relative to the relatively narrow detector.

14. The method as claimed in claim 11, wherein the relatively narrow detector follows the relatively wide detector during scanning.

15. The method as claimed in claim 10, wherein a ratio of the detector data selected and used for reconstruction is matched to a ratio of detector lines of both virtual detectors.

16. The method as claimed in claim 10, wherein twice as many detector lines are used for the relatively wide detector relative to the relatively narrow detector.

17. The method as claimed in claim 10, wherein the relatively narrow detector follows the relatively wide detector during scanning.

18. A tangible computer readable medium including program segments for, when executed on a computer device, causing the computer device to implement the method of claim 10.

* * * * *